United States Patent [19]

Dehlinger

[11] Patent Number: 5,763,263

[45] Date of Patent: Jun. 9, 1998

[54] METHOD AND APPARATUS FOR PRODUCING POSITION ADDRESSABLE COMBINATORIAL LIBRARIES

[76] Inventor: Peter J. Dehlinger, 58 Roosevelt Cir., Palo Alto, Calif. 94306

[ * ] Notice: The term of this patent shall not extend beyond the expiration date of Pat. No. 5,723,320.

[21] Appl. No.: 686,373

[22] Filed: Jul. 24, 1996

Related U.S. Application Data

[63] Continuation-in-part of Ser. No. 563,179, Nov. 27, 1995, abandoned, and Ser. No. 585,365, Jan. 11, 1996.

[51] Int. Cl.$^6$ .................................................. C12M 1/00
[52] U.S. Cl. .................... 435/287; 530/333; 530/334; 435/6; 435/7.1; 436/518; 436/527; 536/25.3
[58] Field of Search ............................... 435/287, 6, 7.1; 530/333, 334, 25.3; 436/518, 527

[56] References Cited

U.S. PATENT DOCUMENTS

| | | |
|---|---|---|
| 4,371,273 | 2/1983 | Kendall et al. . |
| 4,576,477 | 3/1986 | Corbet et al. . |
| 4,683,202 | 7/1987 | Mullis . |
| 4,883,760 | 11/1989 | Heelies . |
| 5,143,854 | 9/1992 | Pirrung et al. . |
| 5,212,979 | 5/1993 | Albrodt et al. . |
| 5,274,240 | 12/1993 | Mathies et al. . |
| 5,324,483 | 6/1994 | Cody et al. . |
| 5,391,785 | 2/1995 | Jones et al. . |
| 5,439,578 | 8/1995 | Dovichi et al. . |
| 5,449,754 | 9/1995 | Nishioka . |
| 5,556,762 | 9/1996 | Pinilla et al. . |

FOREIGN PATENT DOCUMENTS

| | | |
|---|---|---|
| 0 373 203 B1 | 8/1994 | European Pat. Off. . |
| WO 86/00991 | 2/1986 | WIPO . |
| WO 94/27719 | 12/1994 | WIPO . |
| WO 95/11262 | 4/1995 | WIPO . |
| WO 96/33010 | 10/1996 | WIPO . |

OTHER PUBLICATIONS

Fodor et al, Science vol. 251 (Feb. 15, 1991) pp. 767–773.
Bunin, B.A., and Ellman, J.A., "A General and Expedient Method for the Solid Phase Synthesis of 1,4-Benzodiazepine Derivatives," *J. Am. Chem. Soc.* 114:10997–10998 (1992).
Bunin, B.A., et al., "The Combinatorial Synthesis and Chemical and Biological Evaluation of a 1,4-Benzodiazepine Library," *Proc. Natl. Acad. Sci. USA* 91:4708–4712 (1994).
DeWitt, S.H., et al., "Diversomers': An Approach to Nonpeptide, Nonoligomeric Chemical Diversity," *Proc. Natl. Acad. Sci. USA* 90:6909–6913 (1993).
Fodor, S.P.A., et al., "Light–Directed, Spatially Addressable Parallel Chemical Synthesis," *Science* 251:767–773 (1991).
Geysen, H.M., et al., "Use of Peptide Synthesis to Probe Viral Antigens for Epitopes to a Resolution of a Single Amino Acid," *Proc. Natl. Acad. Sci. USA* 81:3998–4002 (1984).

*Primary Examiner*—Paula K. Hutzell
*Assistant Examiner*—Heather A. Bakalyar

[57] ABSTRACT

Method and apparatus for producing combinatorial position-addressable libraries of different-sequence oligomers or different-substituent small molecule compounds are disclosed. The method employs massive parallel synthesis by stepwise subunit addition or substituent addition in a dense capillary-tube array. The libraries allow high throughput screening of library compounds in either solid phase or solution phase, and position-related identification of active library compounds.

12 Claims, 11 Drawing Sheets

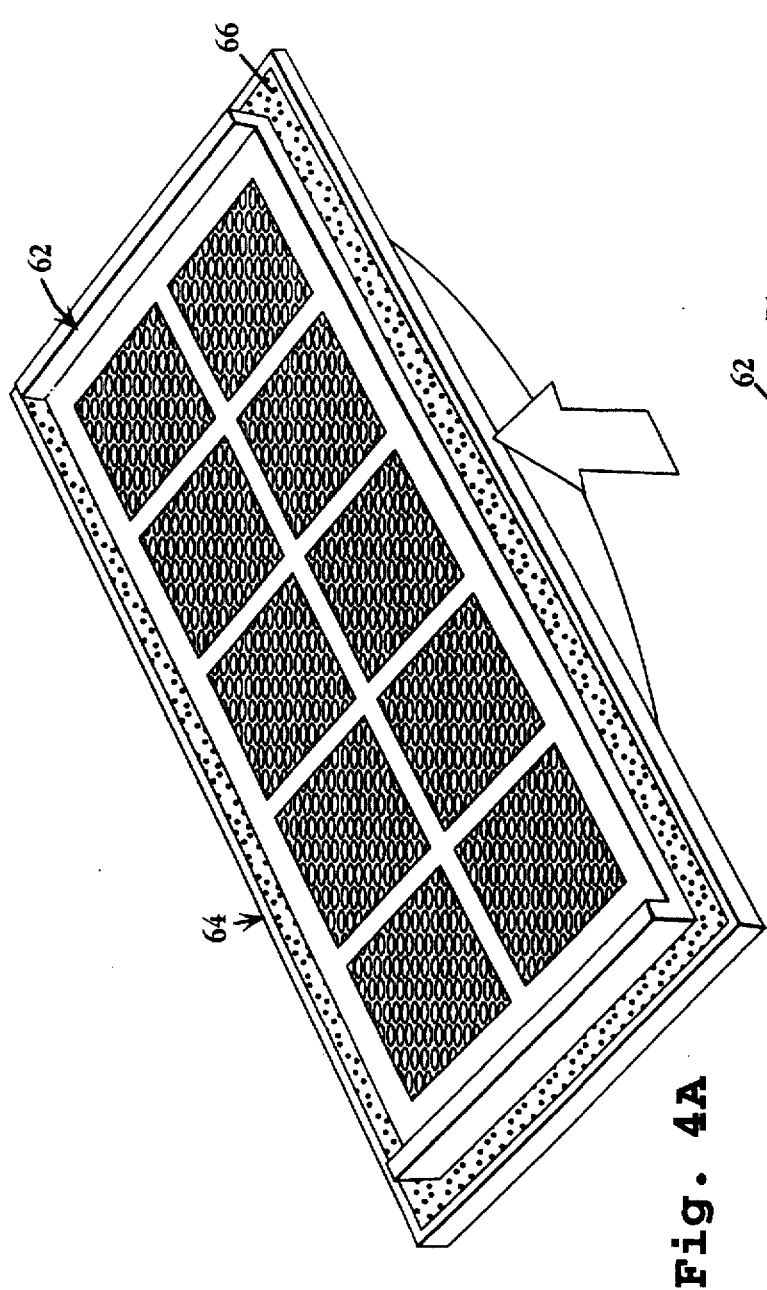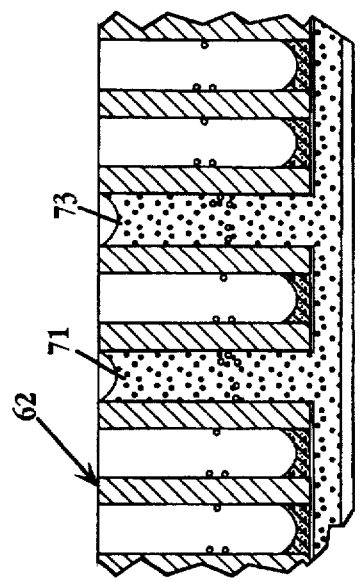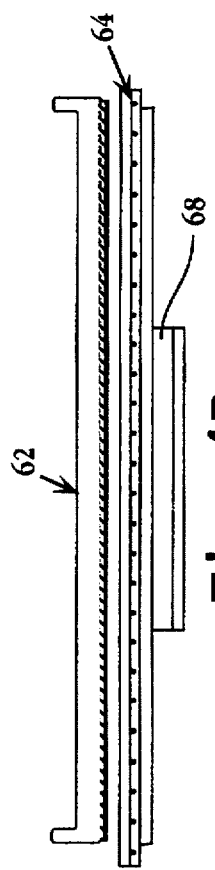
Fig. 4A
Fig. 4B
Fig. 4C

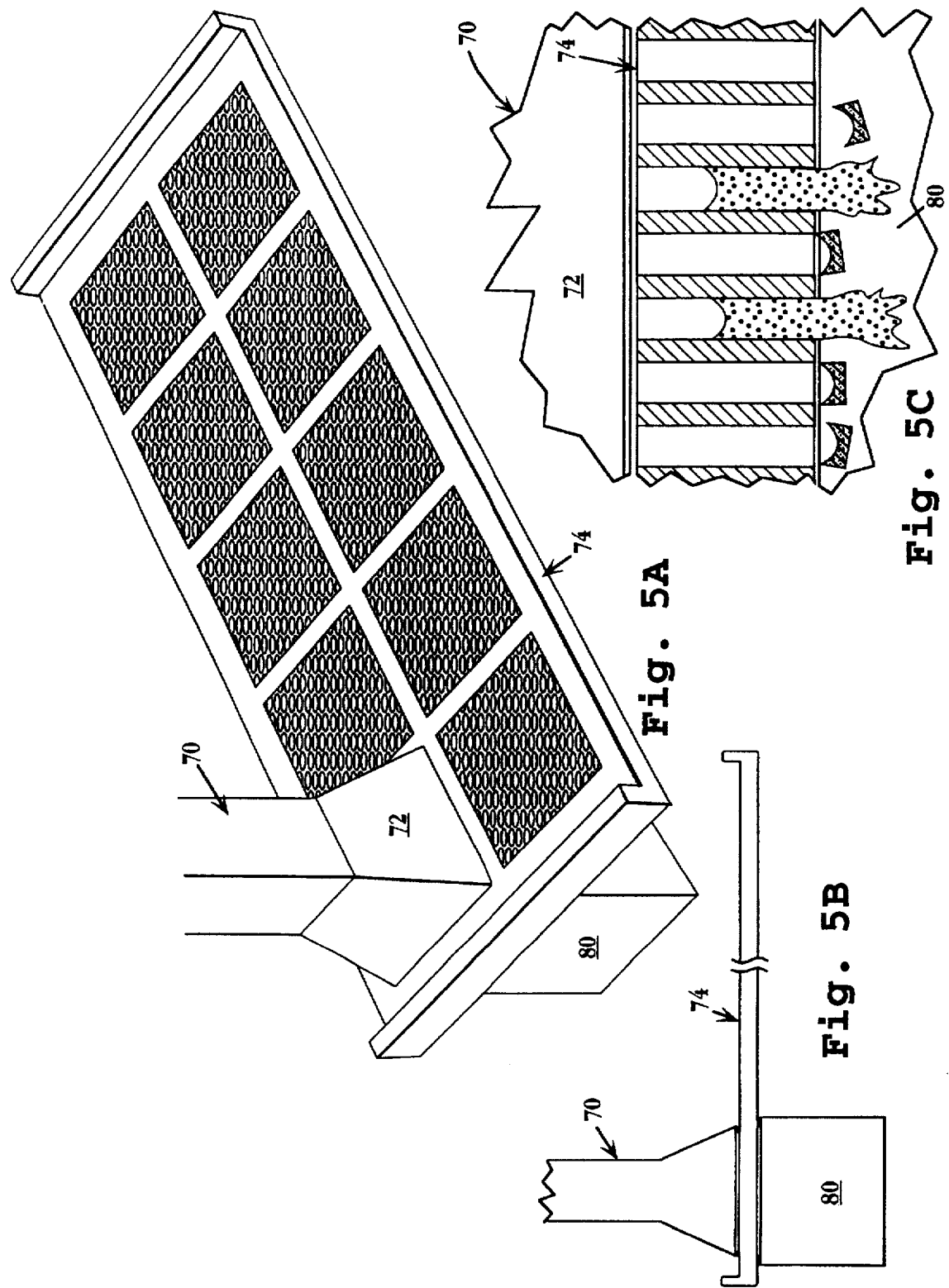

| A | G |
|---|---|
| C | T |

Fig. 7A

| AA | AG | GA | GG |
|----|----|----|----|
| AC | AT | GC | GT |
| CA | CG | TA | TG |
| CC | CT | TC | TT |

Fig. 7B

| CAA | CAG | CGA | CGG |
|-----|-----|-----|-----|
| CAC | CAT | CGC | CGT |
| CCA | CCG | CTA | CTG |
| CCC | CCT | CTC | CTT |

Fig. 7C

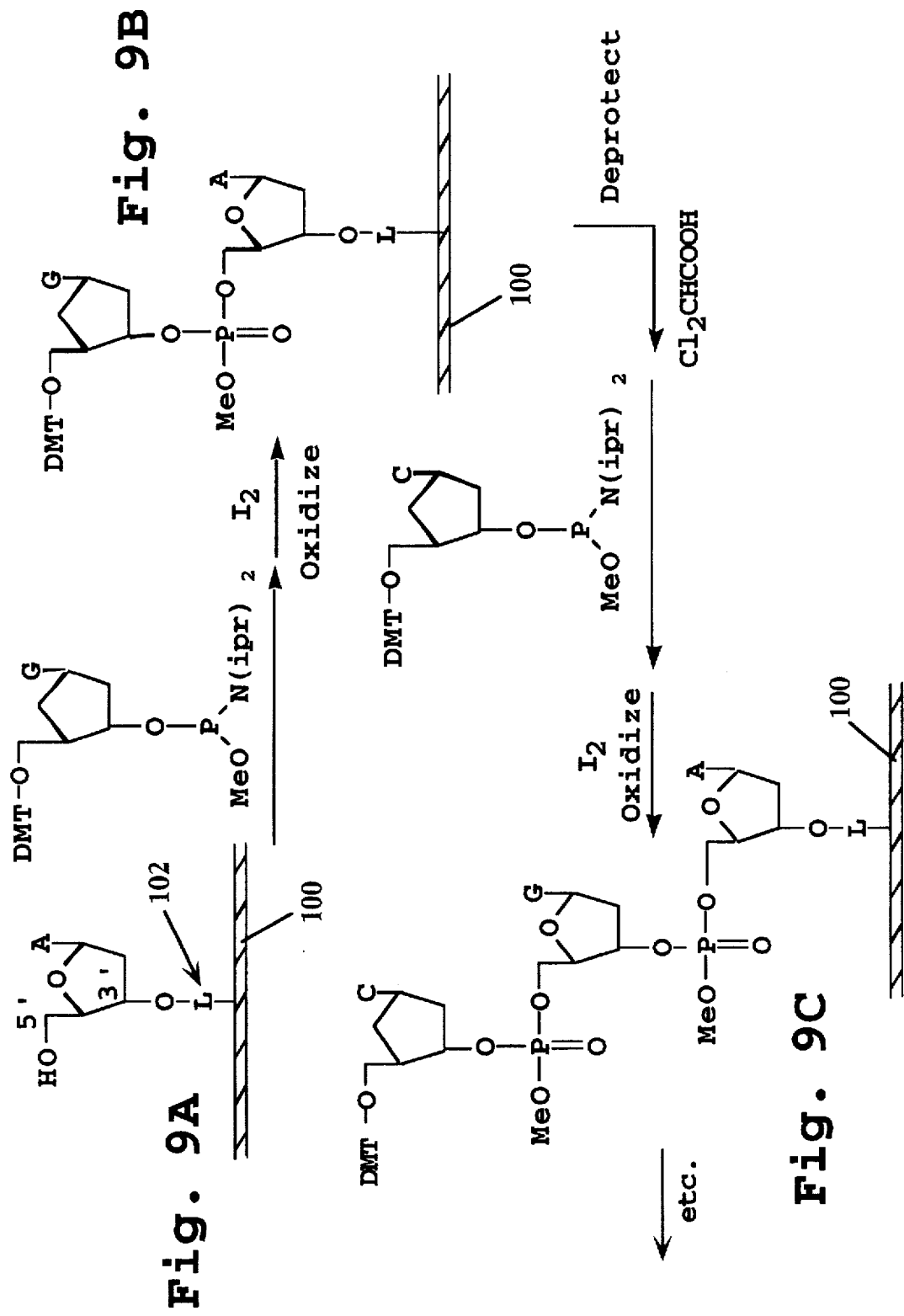

METHOD AND APPARATUS FOR PRODUCING POSITION ADDRESSABLE COMBINATORIAL LIBRARIES

This application is a continuation-in-part of U.S. patent application for "Method and Apparatus for Producing Position-Addressable Combinatorial Libraries", Ser. No. 08/563,179, filed Nov. 27, 1995, now abandoned and U.S. patent application for "Polynucleotide Array Assay and Method", Ser. No. 08/585,365, filed Jan. 11, 1996. Both of these application are incorporated herein by reference.

FIELD OF THE INVENTION

The present invention relates to combinatorial libraries, and in particular, to a method and apparatus for forming and screening position-addressable libraries of oligomers or small-molecule compounds, and to a capillary-tube library device.

BIBLIOGRAPHY OF REFERENCES CITED IN THE SPECIFICATION

Bodansky, M. and Bodansky, A., in *THE PRACTICE OF PEPTIDE SYNTHESIS*, 2nd ed., Springer Verlag, Berlin (1994).

Bunin, B. A., et al., J. Am. Chem. Soc. 114:10997–10998 (1992).

Bunin, B. A., et al., Proc. Natl. Acad Sci. USA 91(11):4708 (1994).

Chen, C. et al., J. Am. Chem. Soc. 116:2661–2662 (1994).

DeWitt, S. H. et al., Proc. Natl. Acad. Sci. USA 90:6909–6913 (1993).

Dillard, L. W. et al., PCT Intl. Appn. Pubn. No. WO 9408051 (4/1994).

Dooley, C. T., et al., Proc. Natl. Acad. Sci. USA 90(22):10822 (1993a).

Dooley, C. T., et al., Life Sci. 52(18):1509 (1993b).

Drmanac, et al., Science 260:1649–1652 (1993).

Eichler, J., et al., Biochemistry 32(41):11035 (1993).

Felder, E. et al., PCT Intl. Appn. Pubn. No. WO 9516209 (6/1995).

Fodor, S. P. A., et al., Science 251:767–773 (1991).

Furka, A., et al., Int. J. Pept. Protein Res. 37:487–493 (1991).

Gait, M. J., Ed., *OLIGONUCLEOTIDE SYNTHESIS: A PRACTICAL APPROACH*, Oxford Univsity Press, Oxford, UK (1990).

Geysen, H. M., et al., Proc. Natl. Acad. Sci. USA 81:3998–4002 (1984).

Geysen, H. M., et al., Proc. Natl. Acad. Sci. USA 82:178–182 (1985).

Houghten, R. A., et al., Nature 354:84–86 (1991).

Houghten, R. A., et al., BioTechniques 13:412–421 (1992).

Kramer, A., et al., Pept. Res. 6(6):314 (1993).

Lee, S.M., in *ENCYCLOPEDIA OF POLYMER SCIENCE AND ENGINEERING*, 2nd Ed., Vol. 3, John Wiley & Sons, New York, 601–615.

Nestler, H. P. et al., J. Org. Chem. 59:4723–4724 (1994).

Pham, E.K. et al., PCT Intl. Appn. Pubn. No. WO 9513538 (5/1995).

Pinilla, C., et al., Biotechniques 13(6):901 (1992).

Pinilla, C., et al., Gene 128(1):71 (1993).

Pirrung, et al., U.S. Pat. No. 5,143,854 (1992).

Sambrook, J., et al., *MOLECULAR CLONING: A LABORATORY MANUAL*, Cold Spring Harbor Press, Cold Spring Harbor, N.Y. (1989).

Southern, E., EP Patent No. 373,203 (1994)

Southern, E., et al., Genomics 13:1008–1017 (1992).

BACKGROUND OF THE INVENTION

Currently there is widespread interest in using combinatorial libraries of random-sequence oligonucleotides, polypeptides, synthetic oligomers and small organic molecules to search for biologically active compounds (Kramer, et al., 1993; Houghten, et al., 1992, 1991; Dooley, et al., 1993a–1993b; Eichler, et al., 1993; Pinilla, et al., 1992, 1993). Ligands discovered by screening libraries of this type may be useful in mimicking or blocking natural ligands, or interfering with the naturally occurring interactions of a biological target. They can also provide a starting point for developing related molecules with more desirable properties, e.g., higher binding affinity.

Combinatorial libraries of the type useful in this general application may be formed by various solid-phase or solution-phase synthetic methods. In one approach, beads containing successive precursors to the target compounds that form the library are alternately mixed and separated, with one of a selected number of reagents being added to each group of separated beads at each step (the "split-mix" method: Furka, et al., 1991; Chen et al., 1994; Pham, et al., 1995; Dillard, et al., 1994). An advantage of this method is that each bead contains only one chemical species, allowing the beads themselves to be used for screening. However, the identity of the species on each bead must be independently determined. Although several methods have been reported for tagging the support beads with molecules more readily analyzable than the library members themselves (e.g., Nestler, et al., 1994; Felder, et al., 1995; Dillard, et al., 1994), the need for separate identification of each species nonetheless limits the usefulness of this approach for the preparation of very large libraries.

Another general approach involves the synthesis of a combinatorial library as a physically segregated array of compounds (Geysen, et al., 1984, 1985; Southern, 1994; Southern, et al., 1992; Bunin, et al., 1992, 1994; DeWitt, et al., 1993). Libraries of compounds have been synthesized on functionalized resins either coated on (Geysen, et al., 1984, 1985; Bunin, et al., 1992, 1994) or contained within (DeWitt, et al., 1993) arrays of pins, with reactions carried out in separate chambers. Southern (1994) used arrays of spots laid down on a substrate such as glass by a pen plotter.

A key advantage of this approach is that the chemical identity of each library element on the array is associated with an addressable position on the array. However, in this method, as well as the split-mix method, preparation of very large libraries would require an inconvenient number of manipulations and/or a large array of separate reaction vessels or sites.

A method for preparation of potentially very high density position-addressable arrays on a planar substrate has been reported (Fodor, et al., 1991; Pirrung, et al., 1992). In this method, thus far applicable only to oligomeric compounds, a substrate having photoprotective groups is irradiated, using photolithographic mask techniques, in selected regions only, to deprotect surface active groups in those selected regions. The entire surface is then treated with a solution of a selected subunit, which itself has a photoprotected group, to react this subunit with the surface groups in the photodeprotected regions. This process is repeated to (i) add a selected subunit at each region of the surface, and (ii) build up different-sequence oligomers at known, addressable regions of the surface.

This method has the advantage that very large permutation libraries, e.g., $10^4$–$10^6$ compounds, can be constructed in a position addressable array by massive parallel subunit addition. For example, the case of oligonucleotide libraries, each subunit addition step requires only four addition reaction, one for each nucleotide added. Thus, a library of oligonucleotide 8 mers (a total of 65,536 compounds) can be constructed with a total of 32 reaction steps (8 subunit additions, 4 reactions each).

In cases where the compounds may be screened for biological activity while still attached to the substrate, this method also allows for massive and rapid screening, by binding a reporter-labeled target to the surface and determining the positions of bound target. Surface arrays of this type may be used both for combinatorial library screening (Fodor, et al., 1995; Geysen, et al., 1984, 1985) or for various types of oligonucleotide analysis, such as sequencing by hybridization (Drmanac, et al., 1993; Southern, 1994; Southern, et al., 1992).

One limitation of this method is in the range of chemical reactions that can be utilized. In general, the photodeprotection chemistry used in the photolithographic approach for making high-density libraries has been limited to chemical modifications that involve stepwise subunit addition, with removal of a single photodeprotecting group before each new subunit addition. Although this chemistry is compatible with synthesis of oligopeptide and oligonucleotides, it is not readily adaptable to many other types of synthetic schemes, particularly those used for making small-molecule libraries.

In addition, large-library planar arrays are necessarily limited in the amount (number of molecules) of each library species, since the planar region available to each species is quite small, e.g., on the order of $10^2$–$10^3$ $\mu m^2$. As a consequence, the ability to detect binding species on the array may be limited. Further, it is not feasible to carry out solution-phase screening on a planar array, because of the difficulty of physically separating different array regions carrying different library members.

It would thus be desirable to provide a method for preparing a large combinatorial library of compounds which has the advantages of (i) massive parallel synthesis of subunits and known, addressable library positions, (ii) adaptable to virtually any oligomer or small-molecule chemistry, (iii) a relatively large area for synthesis of each library member, and (iv) screening of individual library compounds in either solution phase or solid phase.

SUMMARY OF THE INVENTION

In one aspect, the invention includes a method of producing a position-addressable combinatorial library of different-sequence oligomer or different-substituent small molecule compounds. The method includes identifying, in a dense array of capillary tubes, a selected subset of tubes into which a selected one of a plurality of different chemical reagents in a reagent solution is to be introduced, and a complementary subset of remaining tubes in the array. The dense array is preferably a two-dimensional array containing at least 500 tubes, preferably at least $10^3$ tubes, where the tubes have inner diameters of 50 $\mu m$ or less.

The tubes in the complementary subset are blocked, at a selected tube end, and the tubes in the array are then placed in contact with the reagent solution, under conditions effective to draw reagent solution only into the unblocked tubes, preferably by capillarity. The solution drawn into the selected tubes is allowed to react with a wall portion of each tube in a selected subset on which a library compound is being formed.

The steps above are repeated for different subsets of tubes until all the tubes in the array have been reacted, i.e., all the addition reactions for a selected residue position or modification reaction have been carried out. The cassette is then cycled through additional rounds of subunit-addition reactions, until the desired library is produced.

In one preferred embodiment, the tubes in the array are selectively blocked by (i) drawing an polymer solution into at least one end region of the tubes in the array, (ii) selectively injecting a polymer initiator into the tubes in the complementary subset, forming solid plugs in the tubes, and (iii) removing non-polymerized material from tubes in the selected subset. The injecting can be carried out by a position-programmable ink-jet printer head. The polymerizable solution may be, for example, an acrylamide-bisacrylamide solution, where the initiator is persulfate.

In an alternative embodiment, the tubes in the array are selectively blocked by (i) drawing a radiation-polymerizable solution into at least one end region of the tubes in the array, (ii) selectively irradiating the tubes in the complementary subset, forming polymer plugs in the tubes, and (iii) removing non-polymerized material from tubes in the selected subset. The selective irradiating can be carried out, for example, by photomask irradiation or by means of a focused photodiode array.

In still another embodiment, the upper or lower surface of the cassette is covered with a photoablatable sealing film, such as a thin wax film. A focused light beam, such as a focused laser beam, is then be scanned over the array surface, photoablating those laser tubes which are in the selected subset.

The method may be used in forming a combinatorial library of different-sequence oligonucleotides, or analogs thereof, different-sequence oligopeptide or analogs thereof, position-substituted peptides or proteins, polysaccharides with different sequences of saccharide subunits, lipopeptides with different permutations of lipid and/or peptide moieties, glycopeptides with different permutations of saccharide and/or peptide moieties, non-biological oligomers with different-sequence permutations, or small-molecule libraries.

Apparatus for carrying out the method of the above method includes (i) structure for introducing reagent solution in a selected subset of tubes in said array, thereby to effect a compound-addition reaction on the surface of tubes in the selected subset; (ii) structure for removing the reagent solution from the tubes after the reaction; and structure for repeating steps (i) and (ii) until a desired library of compounds, one library compound in each tube, is produced.

In a preferred embodiment, the structure for introducing reagent solution into a selected subset of tubes includes structure for applying a polymer solution to end regions of all of the tubes in the array, structure for selectively polymerizing the tubes in the array which form a complementary subset with the selected tubes of the array, to plug all of the array tubes except those in the selected subset, and structure for introducing reagent solution by capillarity into the unplugged tubes in the array.

In another aspect, the invention includes a position-addressable combinatorial library device having an array of at least $10^3$ capillary tubes, each defining an inner wall portion, and attached to the inner wall portion of each tube, a known-composition oligomer or small-molecule compound, where the array includes at least $10^3$ different known-composition compounds at known array positions.

As above, the device is preferably a two-dimensional array, preferably having at least $10^4$ tubes, where each tube may have an inner diameter of 50 μm or less.

The library compounds in the device may be oligonucleotides or analogs thereof, different-sequence oliogopeptides or analogs thereof, position-substituted peptides or proteins, polysaccharides with different sequences of saccharide subunits, lipopeptides with different permutations of lipid and/or peptide moieties, glycopeptides with different permutations of saccharide and/or peptide moieties, non-biological oligomers with different-sequence permutations, or small-molecule libraries.

In an embodiment for use is solution-phase screening, the library compounds are attached to the wall portions of array tubes through cleavable linkages, such as esterase-cleavable or photolytically cleavable linkages.

In another aspect, the invention includes a method of identifying one or more different-sequence oligomers or different-substituent small molecules capable of interacting with a biological agent, such as a biomolecule, macromolecular complex, or cell. The method includes drawing the agent in a liquid medium into the tubes of a position-addressable combinatorial library device of the type described above, and allowing the agent to interact with the compounds in the tubes. A positive interaction is effective to produce a detectable signal. From the known tube position where such signals are detected, the identity of the compound(s) responsible for the observed signal can be determined.

The method may be carried out in either a solidstate format, in which the agent binds to compounds on the capillary walls, or a solution-phase format, in which compounds in the tube are initially attached to the tube walls through cleavable linkers, and are released into the solution phase of the tube before or after addition of the test agent.

These and other objects and features of the invention will become more fully apparent when the following detailed description of the invention is read in conjunction with the accompanying drawings.

BRIEF DESCRIPTION OF THE DRAWINGS

FIGS. 4A is a perspective view illustrating the imbibing of reagent solution into unplugged tubes in a selected subset of tubes in a capillary-tube cassette in the third station in the apparatus shown in FIG. 1;

FIG. 4B is a side view, in reduced scale, of FIG. 4A;

FIG. 4C illustrates, in enlarged view, the imbibing of reagent solution into unplugged tubes in a capillary cassette;

FIGS. 5A is a perspective view illustrating the removal of capillary tube plugs and reagent solution from a capillary-tube cassette in the fourth station in the apparatus shown in FIG. 1;

FIG. 5B is a side view, in reduced scale, of FIG. 5A;

FIG. 5C illustrates, in enlarged view, the removal of polymer plugs from tubes in a capillary cassette;

FIGS. 7A–7C illustrate exemplary capillary-tube array patterns employed in synthesizing an oligonucleotide library in accordance with the invention;

FIGS. 9A–9C illustrate successive nucleotide addition reactions suitable for producing oligonucleotide libraries in accordance with the invention;

DETAILED DESCRIPTION OF THE INVENTION

I. Definitions

Figure 1:
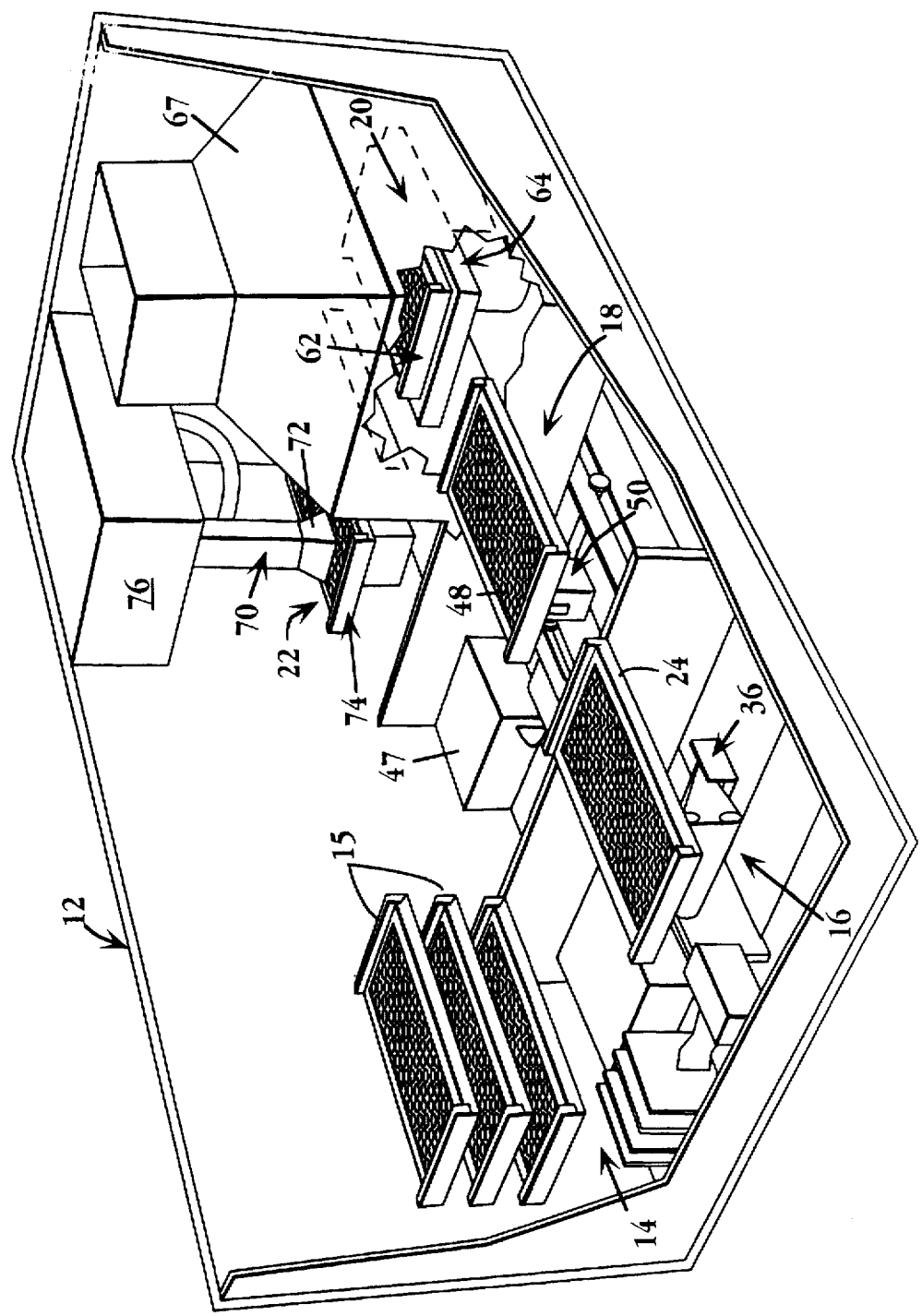
FIG. 1 is a perspective view of apparatus for constructing a capillary-tube combinatorial library device in accordance with the present invention.

The terms below have the following meanings, unless indicated otherwise:

"Combinatorial library" means a library of molecules containing a large number, typically between $10^3$ and $10^6$, of different-sequence oligomers, typically characterized by different sequences of subunits, or a combination of different sequences of side chains and linkages, or different-substituent compounds in a small-compound library.

"Different-sequence oligomer compounds" are oligomers, such as oligonucleotides, oligonucleotide analogs, oliogopeptides, oligopeptide analogs, oligosaccharides, or lipopeptides with different permutations of lipid and/or sequences in the peptide moieties, glycopeptides with different sequence permutations in the saccharide and/or peptide moieties, non-biological oligomers with different-sequence permutations, or different-substituent compounds in a small-molecule library.

The different-sequence oligomers typically have 3–20 residue positions at which the subunit assumes one of a plurality of possible forms, e.g., different nucleotide base or amino acid side chain. Compounds forming a library of different-sequence oligomers may be made up entirely of different-sequence residues, e.g., where the compound contains a total of 3–20 subunits, each having variable subunit forms, or the different sequence residues may be located at defined residue positions within a larger polymer, e.g., at the active or binding site of a polypeptide or protein, or at the sites of known mutation in a polynucleotide gene sequence. Where the different sequences are contained within a larger polymer compound, the different-sequence (variable) residues may be contained within a single, contiguous permuted sequence region, or may made up of spaced residues in a peptide or protein, where each of a number of non-contiguous regions in the peptide or protein are "filled" with one a number of different possible amino acid residues. Thus, "different-sequence oligomer" refers to a relatively small, e.g., 3–20, number of subunit variations, rather than to the size of the compound which contains the oligomer variations.

"Different-sequence small-molecule compounds" are small organic molecules, typically, but not necessarily, having a common parent structure, such as a ring structure, and a plurality of different R group substituents or ring-structure modifications, each of which takes a variety of forms, e.g., different R groups. Such compounds are usually non-oligomeric (that is, do not consist of sequences of repeating similar subunits) and may be similar in terms of basic structure and functional groups, but vary in such aspects as chain length, ring size or number, or patterns of substitution.

A "position-addressable" combinatorial library, in the context of a capillary tube array, is a combinatorial library of compounds, each contained within one of the tubes of the array, where the identity of the compound at each array position is known.

A "polymer solution" is a monomer and/or polymer solution that can be applied as a liquid to an end region of a capillary tube, and which can be converted to a solid polymer plug by addition of a polymer initiator or by irradiation, e.g., by UV, visible, or infrared radiation.

A "dense array of capillary tubes" is an array containing at least about 500 tubes, preferably at least $10^3$, and typically between $5 \times 10^3$ to $5 \times 10^5$ or more tubes, in a spatial array, preferably a planar array, and preferably at a tube density of about $25/mm^2$ or greater.

A "capillary tube" refers to any enclosed structure capable of drawing liquid, particularly water, to a selected tube height by capillary force, preferably to the top of the tube, when the lower tube end is immersed in the liquid. The tube typically has a cylindrical internal shape, although other geometries, such as rectangular spaces formed by closely spaced thin glass plates or coverslips, are contemplated.

II. Apparatus for Producing Position-Addressable, Capillary Tube Combinatorial Libraries FIG. 1 shows an apparatus 12 for producing capillary array libraries in accordance with the invention. The apparatus has a holding area 14 at which capillary-tube cassettes, such as cassettes 15, are held for processing, and four processing stations, 16, 18, 20, 22 at which various cassette operations are carried out.

Figure 2A:
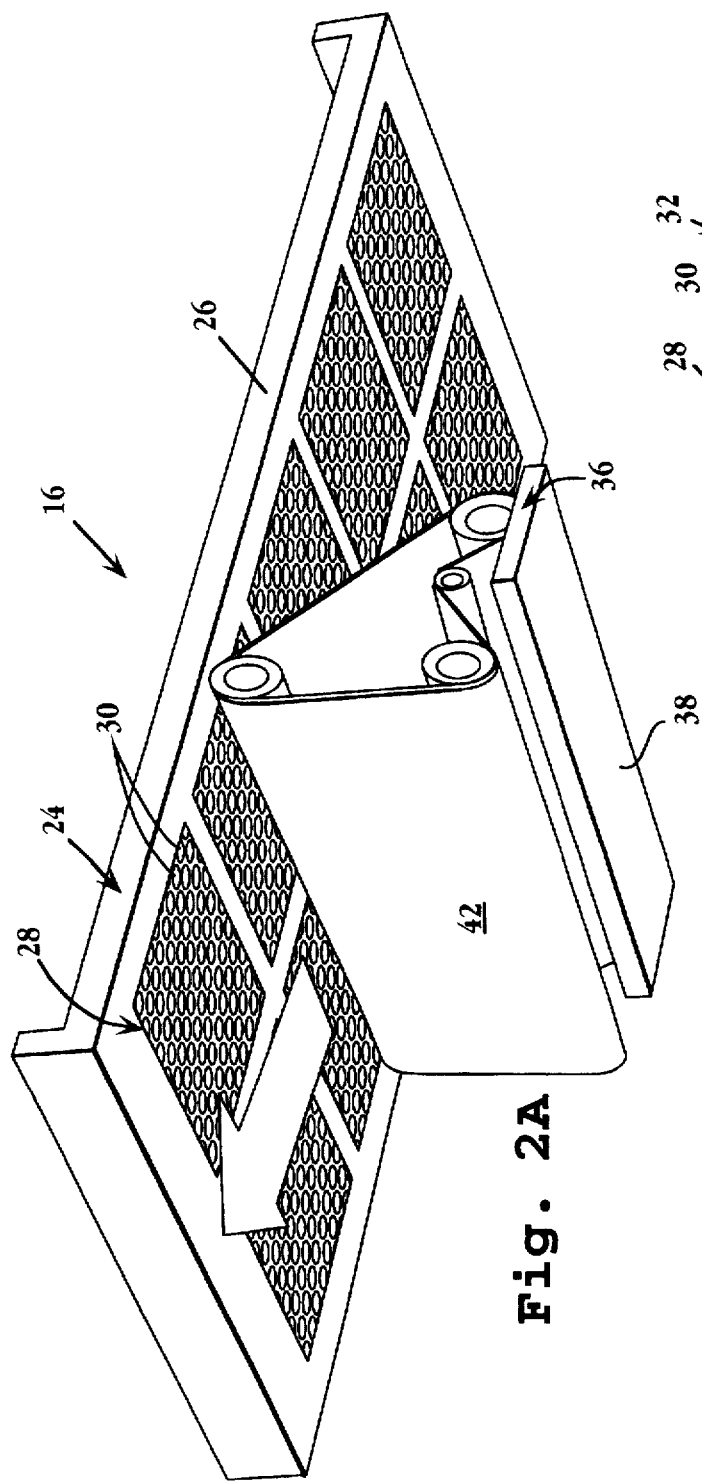
FIGS. 2A is a perspective view showing the operation of a roller applicator in applying a polymer solution to a capillary-tube cassette in the first station in the apparatus shown in FIG. 1.

A typical capillary tube cassette for use in the invention is shown in enlarged view at 24 in FIGS. 2A. With reference to this figure, the cassette includes a tray 26 adapted to support 10 subarrays of capillary tubes, such as the subarray indicated 28. In the embodiment shown, each subarray, such as subarray 28, consists of $10^4$ capillary tubes, such as tubes 30 (the tubes are not shown to scale, and represent many more tubes than are shown). The tubes in each subarray are arranged in a planar N×M array, where N=M=100 in this case. More generally, a capillary tube array in the invention is a dense array containing at least 500, preferably at least $10^3$, and typically $10^4$ to $10^6$ tubes, in a preferably planar, e.g., square or rectangular array. The ten subarrays in cassette form an array of $10 \times 10^4$ or $10^5$ tubes.

The tubes forming the array preferably have the dimensions of tubes such as are commonly used for capillary electrophoresis. Such tubes have an inner diameter of preferably between about 20–200 µm (microns), typically about 50 µm ot less, and outer diameters that are 10–50 µm larger in diameter. i.e., with 5–25 µm wall thickness. For larger arrays, e.g., $10^4$ or larger, the tubes preferably have outer diameters of 100 µm of less, and inner diameters of 50 µm or less. The tubes are cut or otherwise fashioned to lengths of preferably between 0.5 to 3 cm, typically about 1 cm. A typical array formed of tubes having outer diameters of 200 µm, has a density of $25/mm^2$ or greater. Thus, in the cassette shown, each subarray would have an area of about 4 $cm^2$, i.e., less than an inch on a side.

The array, or in the present case, each subarray in the cassette, may be formed by arranging the tubes in a desired, preferably close-packed array, as shown, and bonding the arrayed tubes together in a suitable fashion. The bonding may be done, for example, with a suitable heat-adhesive coating applied to the outer tube walls, followed by heat curing or fixing of the formed array. Alternatively, the tubes may be embedded in a suitable matrix, e.g., an opaque polymer melt or solution, followed appropriate curing or polymerization to form a solid array block. The array block, once formed, may be cut at its upper and lower faces, if desired, to produce a uniform tube-end surface. In one preferred method, relatively thick-wall capillary tubes are ganged together, heated to melt temperature and drawn out to form a unitary structure with thin, weblike separating walls.

Alternatively, the tubes forming an array may be formed, e.g., by laser drilling, as capillary pores in an array bloc, such as a glass or polymer block. In still another embodiment, the tubes may be formed by a series of glass plates, e.g., cover slips, which are separated from one another by spacer elements, typically spacing the plates with a 20–100 µm spacing between confronting walls. The plates themselves may form the array tube elements, or they may additionally having internal ribs which divide each interplate space into a plurality of capillary tubes with rectangular cross sections.

The two opposite tube ends regions of the array are referred to herein as first and second end regions 32, 34, respectively, (see FIG. 2C), which generally form top and bottom end regions the array, respectively. Unless otherwise indicated, each end region is meant to include the end region of each tube in the array; for example, end region 34 is meant to include the lower end region of each tube in the array. Where the method includes selective irradiation of a subset of tube ends in the array (as described below), the corresponding end regions of the tubes in the array may be made opaque with respect to adjacent tubes in the array. That is, light directed into the end region of any tube is blocked from entering the end region of adjacent tubes in the array.

With reference again to FIG. 2A, a cassette in the holding area is moved into the first station (station 16 in the figure) by a suitable conveyor to the applicator position shown for cassette 24. The conveyor (not shown) includes gripping means for holding a cassette by the extended upper ends of the cassette, and conveyor structure for conveying a cassette thus held from one station to another.

Figure 2C:
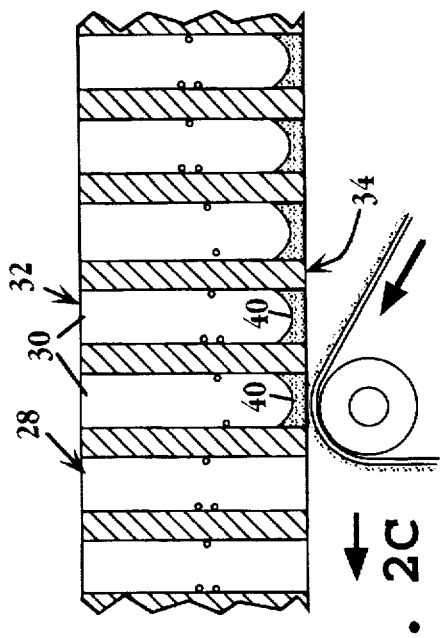
FIG. 2C illustrates, in enlarged view, the uptake of polymer solution into the ends of capillary tubes in the roller operation illustrated in FIGS. 2A and 2B.

In the first station, a roller assembly 36 applies a polymer solution against the lower ends of the tubes in the cassette, to introduce a small quantity of the solution into each of the cassette tubes, as seen in FIG. 2C. The polymer solution may be any of a number of number water-based or solvent-based monomer or polymer materials that can be solidified by polymerization and/or crosslinked by a suitable initiator (Lee). One exemplary solution is an a water-based acrylamide-bisacrylamide solution, such as a 3–20 w/v% acrylamide-bisacrylamide solution containing TEMED (N,N,N',N'-tetramethyethylene diamine), as is commonly used for acrylamide gel electrophoresis (see, for example, Sambrook, 1989, 6.36–6.62). Polymerization can be initiated to introduction of a persulfate solution, at persulfate concentrations commonly employed in acrylamide polymer systems.

Figure 2B:
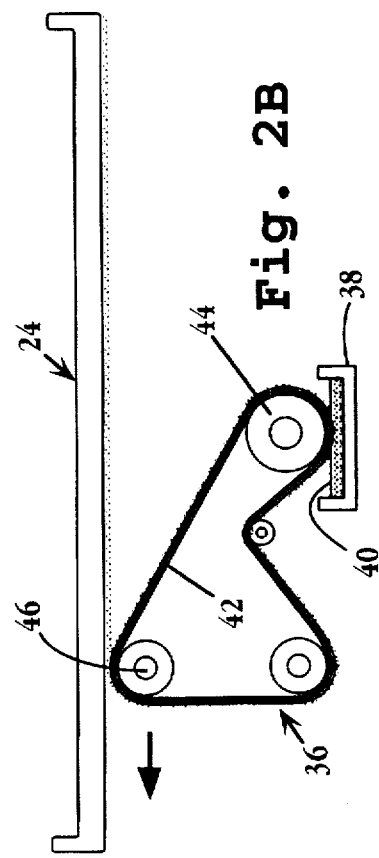
FIG. 2B is a side view, in reduced scale, of FIG. 2A.

The applicator operation carried out in the first station is illustrated in greater detail in FIGS. 2A–2C. Shown in FIG. 2C is a cassette 24 held in the first station, and assembly 36 which is designed to advance along the length of the cassette, in a right to left direction in the figure. With reference to FIGS. 2A and 2B, the assembly includes a tray 38 for holding the polymer solution, indicated at 40 in FIG. 2B. The solution in the tray is picked up by an absorbent applicator belt 42 which is moved in a counterclockwise direction in the figures by a drive roller 44, and three guide rollers, such as roller 46. It can be appreciated from the figures how movement of the assembly across the lower face of the cassette, and the endless-belt movement of the applicator belt from the polymer-solution tray to the lower cassette surface functions to "wet" each of the tubes in the array, that is, apply a small amount of polymer solution 40 to the lower end region of each tube, as shown in FIG. 2C. The amount applied to each tube can be controlled by control of assembly and belt speeds, which are under the control of an electronic control unit 47 in the apparatus. The design and operation of the control unit will be appreciated from the operations of the apparatus described herein.

After the tube wetting operation in the first station, the cassette is moved, under the direction of the control unit, to the second station (station 18 in FIG. 1) where a polymer initiator solution is injected into the lower ends of tubes in a selected, complementary subset of tubes in the cassette, which is here indicated at 48. As will be described more fully below, the operation performed in the second station is intended to selectively block or plug the lower ends of tubes in the complementary tube subset. This is done in apparatus 12 by moving an ink-jet printer head 50 over the lower surface of the cassette, and injecting an initiator solution, e.g., persulfate in the case of an acrylamide solution, into the lower end of each tube which is to be blocked. Details of the injection operation are given in FIGS. 3A–3B.

Figure 3C:
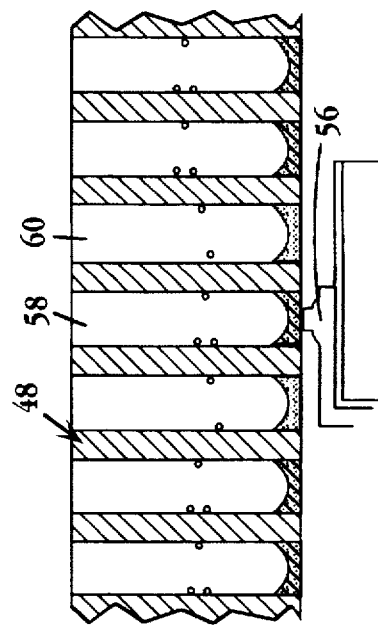
FIG. 3C illustrates, in enlarged view, the injection of initiator solution into the selected tubes in a capillary cassette, to form polymer plugs in those tubes.
Figure 3A:
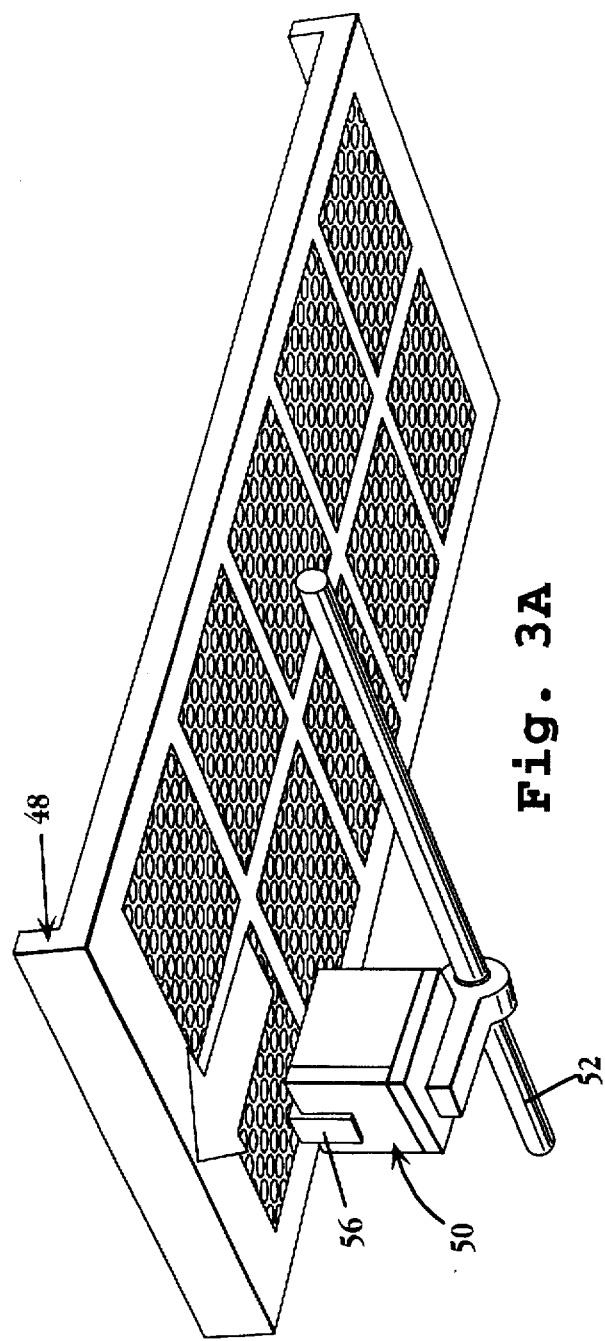
FIGS. 3A is a perspective view showing the operation of an ink-jet printer head in applying a polymer initiator solution to a complementary subset of tubes in a capillary-tube cassette in the second station in the apparatus shown in FIG. 1.
Figure 3B:
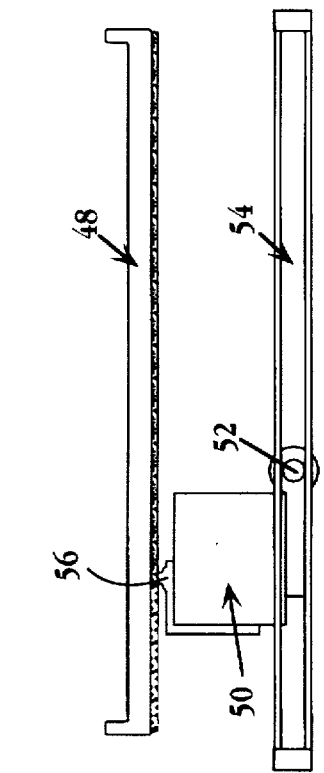
FIG. 3B is a side view, in reduced scale, of FIG. 3A.

As seen in FIGS. 3A–3C, the printer head is carried on a rod 52 which is moved in a longitudinal direction under the control of an actuator, indicated at 54 FIG. 3B, to position the printer head at selected positions along the length of the cassette. The head is also moved along the length of rod 52 under the control of a second actuator (not shown) carried in the printer head housing. Both actuators, which produce a selected x—y printer head motion, are under the control of control unit 47.

An ink-jet emitter 56 in the printer head operates conventional to inject a small volume of polymer initiator at selected cassette positions, corresponding to tube position where polymerization is desired, as the printer head is scanned across the cassette's lower surface. The control unit, which controls the movement of the x and y coordinates of the printer head and the emitter action of the head, is can be programmed conventionally to inject initiator fluid in a selected pattern (corresponding to tubes to be plugged). The construction and operation of the printer head in this mode are conventional, and have been detailed, for example, in U.S. Pat. Nos. 5,467,709 and 5467,116. The printer head resolution may allow multiple injections into each tube to be plugged.

FIG. 3C illustrates with hatch lines the polymerization of polymer solution in selected cassette tubes, as initiator is injected into these tubes, such as tube 58. The polymer solution in the remaining tubes, such as tube 60, which do not receive initiator, remains non-polymerized.

The selection of the subsets of plugged and unplugged tubes, for combinatorial library synthesis will be described below. Briefly, at each subunit addition step, and for each different subunit or compound substituent forming the library, a subset of tubes is selected for that subunit addition. These tubes form the subset of unplugged tubes. The subset of remaining tubes in the cassette forms a complementary subset which is to be plugged. In general, if one of N possible subunits is added at each subunit step, 1/Nth of the cassette tubes are selected for subunit addition, with the complementary set including the remaining N—1/Nth of the cassette tubes. Thus, in the case of oligonucleotide synthesis, where one of 4 different subunits are added at each oligomer position, ¼ of the cassette tubes are in the selected "unplugged" subset, and the remaining ¾ in the tubes in the complementary subset of plugged tubes.

With reference again to FIG. 1, the cassette with selected subsets of plugged and unplugged tubes is now advanced to the third station in the apparatus (station 20) where the lower side of the cassette (such as cassette 62 shown in the figure) is first brought into contact with a blotting pad (not shown) to blot-remove unpolymerized polymer solution from the unplugged tubes in the cassette, then brought into contact with a tray 64 that contains reagent solution that will be imbibed by the unplugged cassette tubes.

The reagent solution imbibed in the unplugged tubes is reacted with wall portions of the filled tubes, to add a selected subunit to an oligomer being formed on the filled tubes, or to produce a selected modification in a small-molecule compound being formed on walls of the filled tubes, as discussed below. As will be discussed below, more than one reagent solution may be added successively to the unplugged tubes. For example, in the synthesis of oligomers with protected end groups, the unplugged tubes may first be exposed to a deprotection solution, e.g., acidic or basic solution. This solution is then removed, e.g., by blotting, and replaced by a reagent solution containing an activated subunit for subunit addition to the deprotected oligomer on the capillary walls. As seen in FIG. 1, the blotting, imbibing and reacting steps are carried out under a hood 67 which is vented through an external vent source (not shown).

Details of the above imbibing step are shown in FIGS. 4A–4C. FIG. 4A shows cassette 62 with a selected set of unplugged tubes, and a remaining set of plugged tubes, formed as above. The cassette is supported in a horizontal position by the above-mentioned conveyor means.

Tray 64 is a shallow receptacle in which is a held the above reagent solution(s), here indicated at 66. As seen in FIG. 4B, tray 64 is held on a support 68 which can be raised and lowered by a piston actuator (not shown) under the control of unit 47. In its raised position, the tray is moved to a position in which the solution in the tray covers the lower end regions of cassette tubes, as shown in FIG. 4C. The unplugged tubes in the cassette, such as tubes 71, 73, then imbibe the reagent solution by capillarity, filling these tubes, as shown, while the plugged tubes remain free of reagent solution.

Although for most sizes of capillary tubes and for most types of reagent solution, capillary forces alone will be sufficient to fill the unplugged cassette tubes, the invention also contemplates applying a differential pressure applied to opposite sides of the cassette, if necessary, to effect or assist tube filling.

The reaction solution in the unplugged, filled tubes is allowed to react with wall portions of the tubes for a time, and under conditions sufficient to complete the next-step synthesis addition or modification used in library synthesis, as discussed further below.

After the desired reaction period, the cassette is moved to fourth and final station 22 (FIG. 1) at which (i) reagent fluid in the unplugged tubes and (ii) the polymer plugs in the remaining tubes are removed, and the tubes are washed. As seen in FIG. 1 and in FIG. 5A, the station includes a nozzle 70 having a head 72 adapted to cover the upper surface of one of the subunit arrays in a cassette, such as cassette 74 shown in the figure. More specifically, the nozzle is adapted to be moved, by a sweep device 76, from subarray to subarray, and to fit in a sealed manner over the top of each subarray. Pressurized gas, e.g., air, is then supplied to the nozzle to discharge reagent solution from the filled tubes and polymer plugs from the plugged tubes, as seen in FIG. 5C. The discharged material is collected in a receptacle 80 (FIGS. 5A–5C) for later waste removal.

To wash the cassette tubes, the cassette may be shuttled one or more times between the third station, where the cassette tubes are filled by capillarity with wash solution and the fourth station, where the wash solution is discharged from the tubes. In this operation, the tray in the third station normally used to supply reagent solution to unplugged tubes contains wash solution which is taken up by all of the tubes in the cassette.

Finally, the washed cassettes are returned to the holding area, from which it will be cycled through the apparatus in accordance with the steps just described.

It will be appreciated from the above that other methods for plugging a selected complementary subset of tubes in a capillary tube array could be employed. For example, in the apparatus described above, the ink-jet printer may be replaced by an optical system for selectively photopolymerizable polymer solution introduced into the bottom regions of the tubes.

The selective polymerization, e.g., with a UV light source, could be carried out through a photomask which is designed to admit light only into the tubes to be polymerized, or by a photodiode array having a pattern of light point sources that are then focused at the plane of the cassette's lower surface, or by a light beam, e.g., laser beam, that is scanned over the cassette surface, to selectively irradiate those tube ends that are to be plugged.

Figure 6:
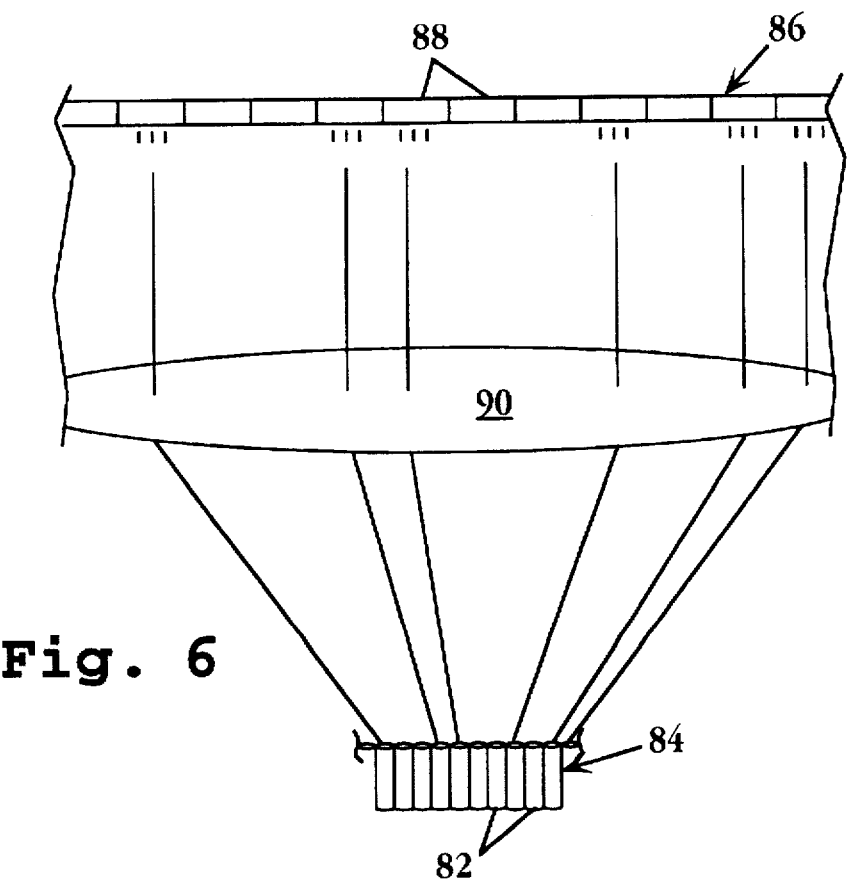
FIG. 6 illustrates a method for selectively irradiating tubes in a capillary tube array by means of a focused light-emitting diode array.

FIG. 6 illustrates a method of selectively irradiating the ends of capillary tubes in a selected subset of tubes, such as tubes 82 in an array 84, where the polymer solution can be photopolymerized. Here the visible light source is a planar array 86 of light emitting diodes (LED's), such as those represented at 88. Each LED can be switched between off and on light-emitting conditions, to form a pattern of light-emissions corresponding to the planar pattern of the complementary tube-array subset whose tube ends are to be blocked. Light-emitting diode arrays suitable for this purpose are well-known, e.g., as described in U.S. Pat. No. 5,449,926.

The pattern of light emissions from array 86 is focused by a condensing lens or lens system, indicated at 90, producing at a focal plane corresponding to the upper surface of the array, a pattern of light beams that is in registry with the pattern of tubes in the selected complementary subset of array tubes, as indicated. An advantage of the LED configuration is that desired light-array patterns needed for the several different subsets used during library production can be quickly and inexpensively generated. One photopolymerization system which is contemplated is an acrylamide-bisacrylamide solution or the type above, using riboflavin as a photo-polymerization inducer.

In still another method for selectively plugging tubes in a dense capillary array, the entire lower surface of the cassette can be covered with a photo-ablatable sealing film, such as a thin wax film. A focused light beam, e.g., a laser beam, is then scanned over the array surface, photoablating those laser tubes which are in the selected "unplugged" subset, and leaving remaining tube end seals intact.

III. Method for Producing Position-Addressable, Capillary Tube Combinatorial Libraries The aim of the method of the invention is to synthesize, by stepwise addition of subunits or chemical substituents, different combinatorial library species in each of the different tubes in a capillary tube array, such as the array formed by the subarrays in the cassette described in Section II.

A. Oligonucleotide Library

For purposes of simplicity, the method will be illustrated initially for the synthesis of an oligonucleotide library having every combination of four deoxynucleoside subunits, e.g., deoxyadenosine (A), deoxyguanosine (G), deoxycytidine (C), and deoxythymidine (T), in a library of octanucleotides, i.e. , a library containing $4^8=65,536$ different-sequence oligonucleotides. In this case, the tube array will include at least $4^8$ tubes, e.g., employing seven of the subarrays in the 10-subarray, $10^5$ tube cassette described above.

At each subunit addition step, the array is divided into four subsets, each containing at least 16,384 tubes, and each intended for subunit addition of one of the four nucleotide bases. For example, at the first subunit addition step, the array may be divided into four 128×128 quadrants, one for each different nucleotide in the first oligomer position, as illustrated in FIG. 7A. Each of these quadrants represents a selected subset, with the remaining tubes in the array, e.g., the remaining 49,152 tubes in the array representing a complementary subset.

As indicated above, the method involves selectively exposing the tubes in each selected subset to a reaction reagent containing one of the four nucleotides, to add that nucleotide to the oligomer being formed on the wall portion in each tube of that subset. Thus, in the case where each subset is one quadrant of the tube array, a reagent solution containing one of the four nucleotides is added selectively to all of the tubes in one of the quadrants, and the solution is allowed to react with the wall portions in those tubes until the nucleotide has been added to the growing oligomer attached to the wall portion. Thereafter, solutions containing each of the other three nucleotides are added successively to the tubes in each of the other three quadrant subsets. As can be appreciated from above, this first-position synthesis requires a total of four cassette cycles, one cycle for each different nucleotide subunit.

At the second subunit-addition step, each of the first quadrants may be divided into four 64×64 subquadrants, one for each different base, as illustrated in FIG. 7B. In this case, the subset of tubes for each different nucleotide is composed of four 64×64 subquadrants, one in each quadrant, and the complementary subset of remaining tubes is composed of the other three subquadrants in each of the four original quadrants. For this subunit addition, reagent solution for each nucleotide base is added successively to each of these four subsets, i.e., in four successive nucleotide addition reactions. As above, and in accordance with the invention, reagent solution is drawn into all of the tubes in each subset, so that only four solution cycles are required to complete subunit addition at the second subunit position.

Similarly, at the third subunit addition step, each of the 16 subquadrants in FIG. 7B is further divided into four equal size (32×32) subquadrants, with each nucleotide subset now being composed of sixteen 32×32 subquadrants, as illustrated in FIG. 7C for the lower left quadrant in FIG. 7B. Again reagent solution for each of the four nucleotides is drawn simultaneously into all of the tubes in the sixteen separate subarrays, so that all four nucleotides can be added with four machine cycles.

This process is repeated until at the final oligonucleotide position, each of the penultimate quadrants, containing 4 members each, is divided into four tubes, such that the subsets for A, G, C, and T addition now each include 16,364 spatially separated tubes, each tube being part of a four-tube subarray. It can be appreciated from FIGS. 7A-7C how this approach leads to the synthesis of a combinatorial library containing every possible 8 mer sequence of deoxynucleotides, and how, by knowing the particular subunit added at each subunit position in each tube of the array, the identity of each individual library member at each tube location in the array is known. The resulting array of library members is also referred to herein as a position-addressable combinatorial library array, in that the identity of each species is known at each array position.

It can also be appreciated that in carrying out the synthesis of an oligonucleotide library of length L, a total of only 4L reagent-addition cycles are required. Similarly, for producing an oligopeptide library of length L, and assuming all 20 common L-amino acids are employed, a total of 20L reagent cycles are required. For carrying out the synthesis of a small-molecule library, where different numbers of reactions, e.g., substituent modifications, are performed at each addition step, the total number of reagent-addition steps required is simply the sum of all of the modification reactions in all of the addition steps.

In the operation of apparatus 12 in carrying out the synthesis cycles, each reaction cycle will require a different subset of selected tubes for reaction and the corresponding complementary subset. In terms of the operation of the apparatus, each cycle will require a different ink-jet printer pattern corresponding to the pattern of tubes to be selectively blocked. These patterns can be readily preprogrammed into the control unit in the apparatus, allowing the apparatus to operate automatically through the desired cycles of preselected patterns.

Figure 8:
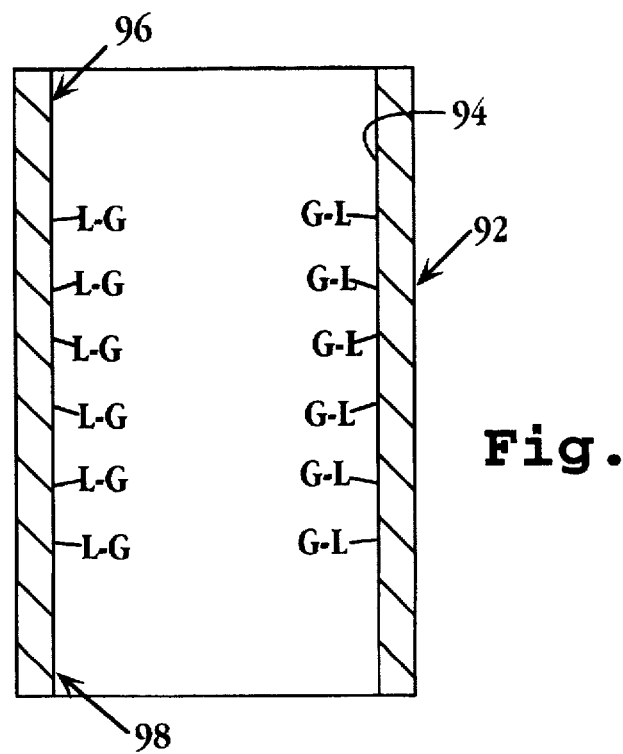
FIG. 8 is an enlarged sectional view of a capillary tube in a tube array, showing a central wall portion with attached linkers on which to build molecules of a library compound.

Turning now to the specifics of the chemistry employed, FIG. 8 is an enlarged section view of tube 92 in a tube array, showing inner wall portion 94 and upper and lower end regions 96, 98, respectively, in the tube. The glass tube has been treated conventionally in its central region to (i) form chemically reactive surface groups, such as carboxyl, hydroxyl, or amine groups on the inner wall portion, (ii) chemically link to the reactive groups, a linker L and a chemical group G which will serve as the chemical platform for solid-phase synthesis of the library compounds on the wall portions of the tubes. Methods for derivatizing glass surfaces for various types of solid-phase synthesis are well known, e.g., U.S. Pat. Nos. 5,436,327, 5,142,047, 5,137,765, and 4,992,383. Suitable linkers terminating in reactive chemical groups are also well known, and are exemplified below. FIGS. 9A-9C illustrate an exemplary synthetic scheme used for preparation of the library of oligonucleotides on the wall portions of glass tubes, in accordance with the invention. In FIGS. 9A-9C, a wall portion of a tube is indicated at 100. The wall portion coating is derivatized conventionally with a linker 102 to which the first nucleotide subunit is then attached. The linker molecules are preferably of sufficient length to permit the compounds in the completed library device to interact freely with molecules to which the device is exposed in library screening, as described below. Longer linkers are also known to lead to more efficient nucleoside coupling reactions (Gait, 1990, p. 45).

The linkage in the present example may be formed by (i) reacting the derivatized glass surface with a long chain bifunctional reagent such as a diol, diamine, ethylene glycol oligomer or amine-terminated ethylene glycol oligomer; (ii) reacting the free hydroxyl or amino end of the linker with the first nucleoside, which is activated as the phosphoramidite, and (iii) oxidizing of the resulting linkage to a phosphotriester or phosphoramidate linkage, respectively. The phosphotriester will be converted to a phosphate linkage after oligonucleotide synthesis is complete. In either case, the substrate-to-oligonucleotide linkage is base stable, and the oligonucleotides will thus remain bound to the substrate throughout the deprotection steps which conclude the synthesis. This issue has been addressed by Southern and Matson, inter alia, and the above linking steps are analogous to those described in these references.

Each nucleoside added in the synthesis is 5'-protected, preferably by a dimethoxytrityl (DMT) group. The exocyclic amino groups on the purine and pyrimidine bases of the nucleosides are also protected, as amides, throughout the sequence, according to well established methods (Gait, 1990), and can be deprotected by treatment with ammonia upon completion of the library synthesis. Because the coupling reactions are sensitive to air and moisture, they are preferably carried out under an inert atmosphere.

In the exemplary reactions shown, the first attached nucleoside is 5'-deprotected at this stage by treatment with dichloroacetic acid, in accordance with well known methods. The deprotection step, at each subunit addition stage, can be carried out simultaneously on all of the tubes in the array, or can be applied selectively to each subset of "unplugged" tubes, as described above. In the former case, a cassette in apparatus may be moved directly from the holding region to station 18, where deprotection solution is imbibed by all of the cassette tubes. After the deprotection reaction, and removal of the deprotection solution from the cassette tubes, the tubes may be washed, as above, and then cycled through the N different subunit steps, as above. After addition of all N subunits, the cassettes is then ready to be recycled through another round of deprotection and N different subunit addition steps.

The second nucleoside unit, deoxyguanosine, is introduced in activated form as the 3'-phosphoramidite, protected at the 5'-hydroxyl by a DMT group. The coupling reaction forms a phosphite triester linkage between the two nucleosides, which is oxidized by iodine to the more stable phosphotriester (FIG. 9B).

It is a recommended practice in oligonucleotide synthesis (Gait, 1990) to cap any unreacted 5'-hydroxyl groups remaining after each coupling step by treatment with acetic anhydride. This effectively terminates the chain and ensures that subsequent reactions proceed only by propagating chains of the desired sequences. However, this step may not be necessary if a large excess of nucleoside phosphoramidite to reactive sites is used (Southern, 1994).

After 5'-deprotection, a third similarly activated and protected nucleoside (deoxycytidine) is added, giving the trimer (FIG. 9C) after oxidation. These steps are repeated with further nucleoside units until the desired oligonucleotides have been formed on the tube wall portions. At this point, the terminal 5'-hydroxy groups are deprotected with dichloroacetic acid as before. Finally, the methyl groups on the phosphotriester linkages are removed by treatment with thiophenol or ammonia, and the purine and pyrimidine bases are deprotected by treatment with ammonia, all according to known methods (e.g., Gait, 1990). These final treatment steps may, of course, be carried out simultaneously on all tubes in a cassette, as above.

The members of the oligonucleotide library illustrated above consist of contiguous sequences of different-base residues. Alternatively, the different base residues may be introduced at selected positions in polynucleotide fragments, e.g., at known mutation positions in a DNA sequence corresponding to a known gene. In this embodiment, all of the tubes in the array are first reacted with a DNA sequence corresponding to the first "common-sequence" region of the coding region, followed by one or more subunit addition reactions of the type described above to add different-sequence nucleotides at each of the selected subsets of tubes in the array. These variable positions may include a segment which consists of, e.g., a variable-sequence six-nucleotide fragment, followed by a second common DNA fragment which is attached to each tube in the array, at the end of the variable region, or alternatively, a series of different-sequence positions, e.g., six separate positions, separated by extended-length common-sequence regions.

For example, the library may be created to encompass a large number, e.g., $10^3$, of possible permutations of mutations over a long stretch of coding region, or it may be designed to introduce a large number of variable sequences at or near the active site residues of ribozymes, for selection of high activity ribozymes.

The above reaction steps produce oligonucleotides having a 3' proximal to 5' distal orientation. Alternatively, the nucleotide subunit addition reactions may be carried out in a manner that produces 5' proximal to 3' distal orientation, employing the subunit addition reactions detailed in co-owned U.S. patent application for Position-Addressable Polynucleotide Arrays, Ser. No. 08/520,730, filed Aug. 29, 1995, and incorporated herein by reference. As described in the referenced application, oligonucleotide arrays of this type may be used for constructing position-addressable arrays of extended DNA sequence fragments, probes, or genes.

B. Polypeptide Library

This section describes the synthesis of a position-addressable tetrapeptide library having $1.6 \times 10^5$ different-sequence members, each carried on a capillarytube wall portion at a known position in a tube array.

Figures 10A, 10B:
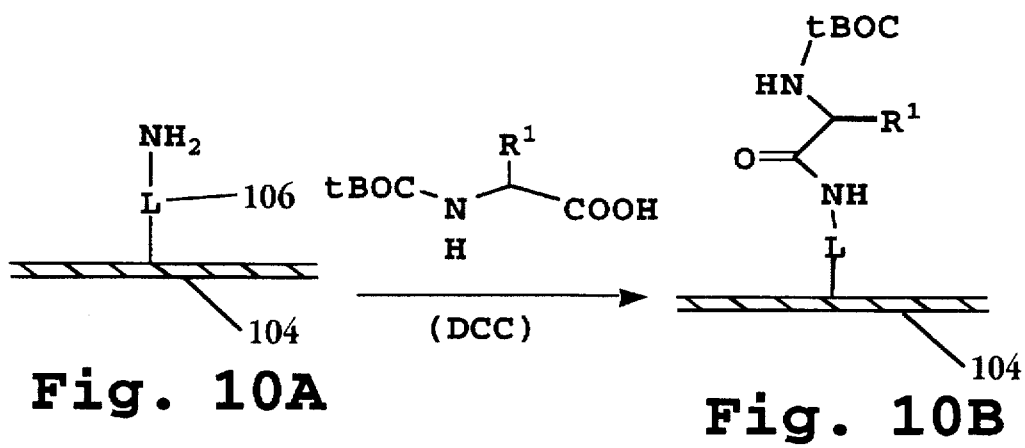
FIGS. 10A–10C illustrate successive amino acid addition reactions suitable for producing oligopeptide libraries in accordance with the invention.
Figure 10C:
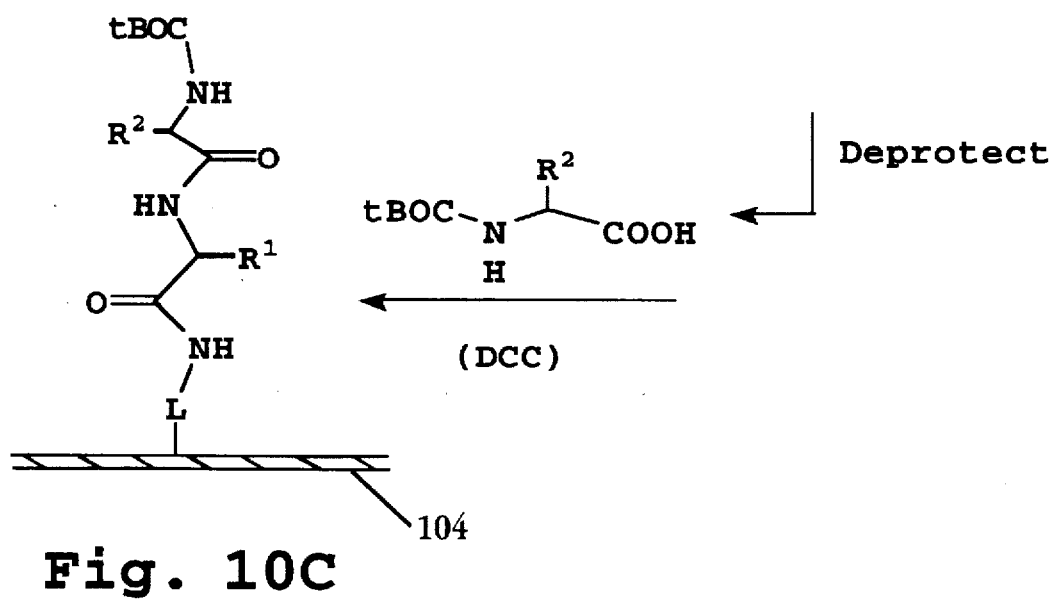

FIGS. 10A–10C illustrate attachment of the first sequence of amino acids to tube wall portion, here shown at 104, derivatized with a linker "L" 106 terminating in an amine group. The linker may be, for example, a diamine or an amine-terminated ethylene glycol oligomer, as described above for the preparation of an oligonucleotide library.

According to well known methods of solid phase peptide synthesis (e.g., Bodansky and Bodansky, 1994), the first amino acid is added, together with an activating agent, preferably dicyclohexylcarbodiimide (DCC), and is thus attached to the free amino end of the linker group, above. The amino group of the incoming amino acid is protected, preferably with the t-butoxycarbonyl (TBOC) group (FIG. 10B). Deprotection of the terminal amino group, by treatment with dilute acid, is followed by addition of the second protected amino acid, giving the dipeptide, shown in FIG. 10C. These steps are repeated until the desired library composition has been achieved, and the final amino protecting group is removed, again by treatment with dilute acid.

As above, three basic types of sequence-variation libraries are contemplated. In the first, the libraries are composed of oligopeptides composed of, for example, 4–10 residues having two or more amino acid variations at each residue position. These libraries are formed by successive subunit-addition reactions in various selected array tubes. Libraries of this type are useful, for example, for identifying antigens or peptide effectors that show high-affinity binding to a selected antibody or receptor site. In designing libraries of this type, the degree of amino acid variation may be dictated by the amino acid residue at a known antigen. That is, each residue may be limited to 2–4 different amino acids having physico-chemical properties similar to the amino acid at that position in a known antigen, thus significantly expanding the length of library oligopeptides that can be made with a given size tube array.

In a second general type of library, the amino acid variation is confined to a selected contiguous region, e.g., a contiguous region in the active site in an enzyme or in the binding site in an antibody. Here the tubes in the array are first reacted with one end terminal portion, e.g., the N-terminal portion of the larger peptide or protein, followed by successive subunit addition reactions in the variable-sequence region, as above, followed by reaction of the tube array with the other end region of the larger peptide.

In a third general type of peptide library contemplated herein, the amino acid variation is at selected, spaced residue positions within a larger peptide or protein, typically at three or four non-contiguous residue positions known to define the active site in an enzyme, or the binding site in an antibody. Here all of the array tubes are first reacted with one end terminal portion, e.g., the N-terminal portion of the larger peptide or protein, followed by subunit addition reactions in the variable-sequence region, as above, followed by reaction of a second multi-residue common region of the larger peptide, followed by subunit addition reactions in the next variable-position residue, and so forth until the entire library is formed.

Both of the latter-type libraries are useful in protein engineering studies designed to identify amino acid changes that enhance a selected protein or polypeptide property, such as binding affinity or enzyme activity. Methods of screening such protein libraries are considered below.

C. Small-Molecule Library

Also contemplated in the invention are position-addressable libraries of small-molecule organic compounds, such as benzodiazepines-- having a large number of parent compound R-group substitutions. The general synthetic scheme follows the methods described by Bunin and DeWitt, who prepared libraries of, respectively, 40 and 192 different benzodiazepines by solid-phase methods on arrays of pins. Briefly, at each successive synthetic step, one of a plurality of different selected substituents is added to each of a selected subset of tubes in an array, with the selection of the tube subsets being such as to generate all possible permutations of the different substituents employed in producing the library. One suitable permutation strategy is outlined in co-owned patent application for Method and Apparatus for Producing Position-Addressable Combinatorial Libraries, Ser. No. 08/512,027, filed Aug. 7, 1995, and incorporated herein by reference.

It will be appreciated that the general permutation strategy just outlined can be applied to the synthesis of any small-compound library which can be constructed by successive addition, at each addition step, or one of a plurality of substituents, i.e., reactants used in successively constructing the small-molecule library member compounds. Further, the method may utilize, for linking the small-molecule compounds to the tube wall portions, a linker that can be cleaved chemically, e.g., a disulfide linker, enzymatically, e.g., an ester or amide linker, or photolytically, to release the small molecule from the wall tube wall portions final library synthesis, for screening methods such as described in the section below.

IV. High-Throughput Library Screening Methods

This section describes high throughput screening methods for identifying oligomeric or small-molecule library compounds capable of interacting specifically with a selected biological agent, such as a biomolecule, macromolecule complex, or cell, employing a combinatorial library device of the type described above.

In the method, each member of the library is screened for its ability to interact specifically with the selected agent. Representative types of biomolecules include (i) a complementary-sequence DNA or RNA molecule in the case of an oligonucleotide library, for use in sequencing by hybridization of the RNA or DNA molecule, (ii) an analyte gene or gene fragment, for use in detecting one or more of a large number of possible mutations in the analyte ligand, (iii) an antibody or receptor protein, in the case of an oligopeptide library, (iv) a ligand or enzyme substrate in the case of an antibody or enzyme library, and (v) an enzyme or receptor in the case of a small-molecule library.

Representative kinds of macromolecular complexes include ribosomal/RNA complexes, DNA/DNA binding agents, such as DNA complexes with a polymerase, transcription factor, initiation factor, or termination factor, multienzyme complexes, subcellular membrane complexes, e.g., containing membrane bound receptor proteins, and viral or subviral complexes. Representative cells for use as biological agents include isolated bacterial cells, eukaryotic microorganisms, and isolated plant or animal cells.

In practicing the method, the biological agent is drawn into the compound-containing tubes, and allowed to interact with the individual library compound in each tube. This interaction is designed to produce a detectable signal that can be used to monitor presence of the desired interaction. As examples, in the case where the biological agent binds to a selected library compound attached to a capillary wall, the detectable signal can be produced by any detectable reporter, e.g., a fluorescent reporter, carried on the biological agent. Alternatively, where the biological agent, e.g., an enzyme, or cell, or subcellular fraction, is capable of converting a substrate to a detectable signal, the detectable signal would be produced by adding the substrate to the capillary tubes, after binding the biological agent to the capillary walls containing the desired library species. Exemplary types of detectable signals for use in a solution-phase format are considered below.

For purposes of illustration, this section will first consider the method in a solid-phase format for selecting an library oligopeptide which has a high binding affinity for a ligand antibody. The antibody, which forms the biological agent in the method, is labeled conventionally with a fluorescent reporter.

Figure 11A:
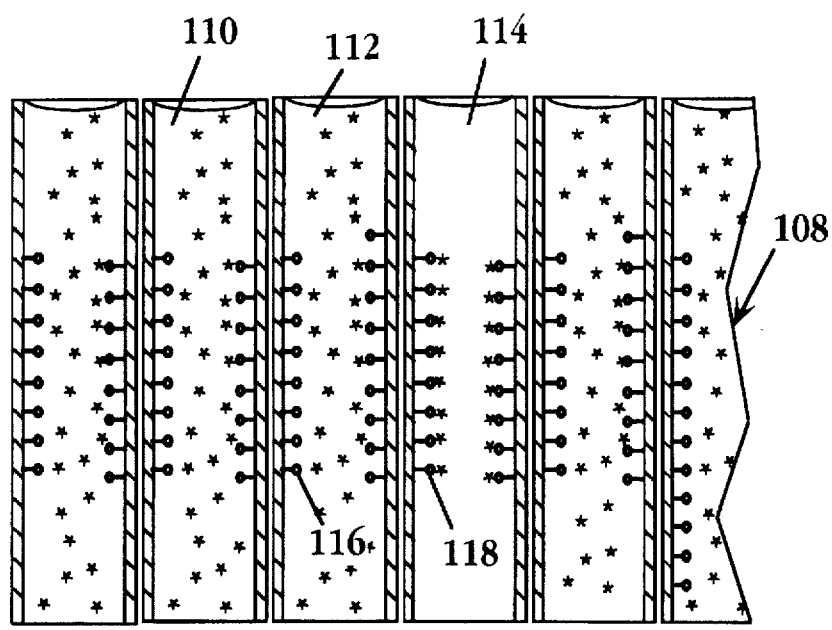
FIGS. 11A and 11B illustrate steps in screening a library formed in a capillary tube array, in a solid-phase format in accordance with the invention.
Figure 11B:
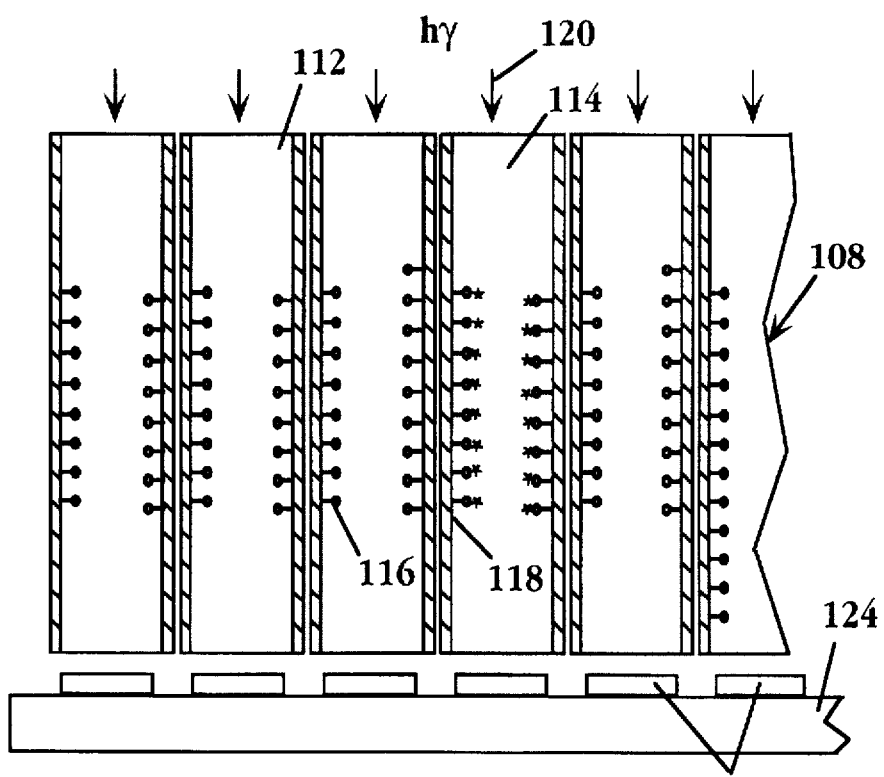

FIGS. 11A and 11B show, in cross-sectional view, a fragmentary portion of a position-addressable capillary-tube array device 108 constructed according to the invention. The device includes a row of capillary tubes, such as tubes 110, 112, 114, each tube having a known-sequence combinatorial library compound, such as indicated at 116, 118 in tubes 112, 114, respectively, attached to the tube's inner wall portion.

In the assay method, an aqueous solution 120 of the biological agent—in this case, a fluorescent-labeled antibody—is drawn by capillarity into each of the tubes. The labeled antibody is here indicated by "*" symbols. The solution is allowed to react with the library compounds under conditions in which the antibody can bind specifically and with high affinity to oligopeptides in the library which form epitopes recognized by the antibody. In the figure illustrated, the library compounds in tube 114 bind the antibody, but other library compounds (carried in the other array tubes) do not, leading to fluorescent labeling of the wall portion in tube 114 only. The capillary array is now treated to remove the antibody solution, and may be washed to remove non-specifically bound antibody, e.g., by drawing wash solution into the array tubes, and treating the array, e.g., by blotting, to remove the wash solution.

The array can be analyzed for identification of tubes having bound fluorescence by conventional methods, e.g., as illustrated in FIG. 11B, which shows tube array 108, a fluorescence excitation beam 122 which directs light through each of the tubes in the array, and a photodetector array 124, such as a conventional photodiode array. The photodetector includes a planar array of photodiode detector elements, such as elements 126, which correspond in positions to the array tubes, as indicated. Position detection of one or more tubes with bound fluorescence is then determined from the optical input from each photodiode. Alternatively, the array may be scanned by a conventional confocal fluorescence microscope device, where the array is carried on a movable stage for movement in a X—Y plane as the array tube elements are successively aligned with the beam, as discussed in above-reference U.S. Pat. application Ser. No. 08/512,027.

Alternatively, after binding labeled antibody to antibody-specific library compounds in the array, and washing the tubes, the tubes may be emptied and refilled with a denaturing solution, e.g., a high-salt solution, capable of releasing specifically bound antibody in the one or more tubes containing labeled antibody. The capillary array is then evacuated, e.g., by aspiration, over a membrane held tightly against the evacuated side of the tubes. By using a membrane capable of capturing the released agent, there is formed a 2-dimensional representation of the capillary array, with each position on the membrane corresponding to a known capillary array position.

The membrane can be scanned, e.g., by conventional methods employing a confocal, scanning fluorescence microscope, to determine the capillary array positions of array positions at which signal is detected. Even if some spatial resolution is lost in the transfer method, the location of observed signal will allow one to select the desired library compound from a small number of compounds clustered in a known array area. As another example, for use in protein engineering, or in the development of artificial enzymes, the library members are proteins having permutations of amino acids at selected residue positions, as outlined above, or nonpeptide oligomers that have the potential, as artificial enzymes, to catalyze the conversion of a selected substrate, which is the target agent. The substrate is selected so that catalytic activity is accompanied by the production of a detectable signal, e.g., using as a substrate, one that is converted to a detectable product.

As another example, the method may be employed for sequencing by hybridization (SBH) or other DNA sequence analysis methods involving binding of reporter-labeled target analyte DNA to selected oligonucleotides in position-addressable oligonucleotide library (Southern, 1994; Southern, et al., 1992; Pirrung, et al., 1992; Drmanac, et al., 1993). The present method provides the advantage over DNA analysis methods that employ planar arrays of positional addressable oligonucleotide libraries, in that the total amount of library material can be significantly greater in a capillary tube than on a planar array. For example, the total wall surface area of a 2 cm long capillary tube having a 50 µm inner diameter is about $10^3$ greater than the surface area defined by the cross-sectional area of the tube. Because of this greater surface area, and correspondingly greater amount of library material at each position, an amplification factor related to the amount of target binding allowed to any library species of up to several orders of magnitude can be achieved.

It will be appreciated how the solid-phase method just described can be adapted for use with more complex types of biological screening agents. For example, to screen for oligopeptides capable of binding to the surface of intact cells, a suspension of cells having surface binding receptors are added to the tubes, which are then washed to remove unbound cells. The cells may be pre-labeled with a detectable reporter, stained after binding to the library species, or the bound cells in the tubes may be exposed to a substrate, after washing the tubes, to produce a detectable signal. Alternatively, the tubes may be treated to release specifically bound cells, which are then "plated" on a cell-adhering membrane, and examined, e.g., microscopically, for the presence of cells.

According to another important aspect of the invention, the capillary-tube array can be used for a variety of solution-phase high-throughput screening methods, since each library member is formed in a separate capillary tubes, i.e., reaction chamber. In this general embodiment, the library members are formed on the walls of the tubes linked to the tube walls through a cleavable linker. The linker may be photocleavable, enzymatically cleavable, e.g., an ester bond, or chemically cleavable, e.g., a disulfide bond. The only limitation to the selection of cleavable bond is that it be compatible, i.e., resistant to, the chemistry employed in library synthesis.

Figure 12A:
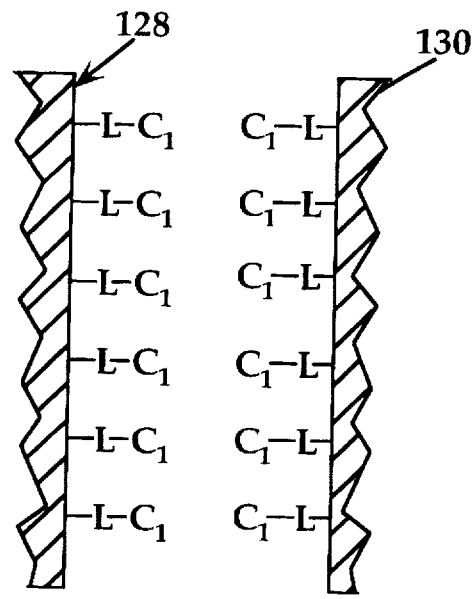
FIGS. 12A and 12B illustrate steps in screening a library formed in a capillary tube array, in a solution-phase format in accordance with the invention.
Figure 12B:
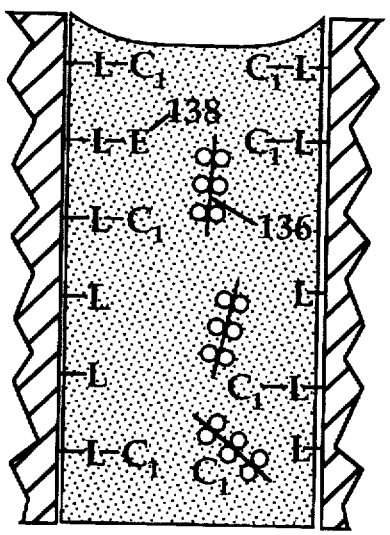

FIGS. 12A and 12B show representative tubes in a library used in solution-phase synthesis, in accordance with the invention. The method illustrated is designed to identify one or more small-molecule library compounds capable of inhibiting or blocking translation in a cell-free system, such as a reticulocyte cell free system, capable of translating exogenous messenger into coded-for polypeptides.

FIG. 11A shows a tube 128 in a dense capillary array of tubes, where the library compounds, such as indicated at $C_1$, are formed on the tube walls through attachment to an ester-containing linkage, such as indicated at 134. The biological agent which is drawn into the capillary tubes in this case includes components of a cell-free extract containing an exogenous mRNA (indicated by the polysomal structures such as shown at 136 in FIG. 12B) and a radiolabeled amino acid, and an esterase enzyme, such as indicated at 138 in FIG. 12B, capable of cleaving the linkers and releasing the library compounds into solution phase.

After a suitable incubation time, e.g., 30 minutes at 37° C., polypeptides in the tubes are precipitated, e.g., by addition of a small amount of trichloroacetic acid at one tube end, or by heating, and the tube contents are aspirated onto a filter, forming a two-dimensional position-addressable pattern, as above, that can be analysed by conventional autoradiographic methods, to detect array positions at which translation was inhibited, as evidenced by a lower density of film exposure.

The method is adaptable to a variety of other types of solution-phase screening. For example, in the method just described, the effect of small molecules on some cell function could be similarly assessed, by employing target cells in the tubes, and examining the cells, e.g., on a 2-dimensional array, or after replica plating such an array onto an agar plate, for changes in the selected activity.

rom the foregoing it will be appreciated how various objects and features of the invention are met. The method allows for massive parallel synthesis of library compounds, by successive filing and draining of large groups of capillary tubes, and very large libraries, in the range up to $10^6$ or more can be produced, limited only by the size of the capillary tube array. Further, because the tubes in the array can be extended in length to accommodate greater amounts of library material, both large libraries and adequate library material can be achieved.

The capillary tube format is compatible with both oligomer and small-molecule synthesis, since virtual any solvent and reaction conditions may be selected, and reaction does not involve photoactivation or photodeprotection chemistry. Further, both solid-phase and solution-phase screening formats are possible, since each of the tubes provides an isolated chamber for reaction between library molecules and the test material.

Finally, identification of screened library compounds is rapid and efficient, requiring only that the position of tubes containing molecules of interest be determined, e.g., by fluorescence scanning.

Although the invention has been described with respect to particular spool structures, methods, libraries, and library devices, it will be appreciated that various changes and modification can be made without departing from the invention.

It is claimed:

1. A method of producing a position-addressable combinatorial library of different-sequence oligomer or different-substitiuent small molecule compounds, comprising the steps of:

(i) identifying, in an array of capillary tubes, a selected subset of tubes into which a selected one of a plurality of different chemical reagents in a reagent solution is to be introduced, and a complementary subset of remaining tubes in the array, (ii) selectively plugging a tube end of each capillary tube in said complementary subset, (iii) placing ends of the tubes in said array in contact with said solution, under conditions effective to draw solution into the unplugged tubes only, (iv) allowing the solution in the tubes in the selected subset to react with a wall portion of each tube on which a library compound is being formed, (v) unplugging the plugged tubes, and (vi) repeating steps (i)-(v) for different subsets of tubes and reagent solutions until said library is produced in said tubes.

2. The method of claim 1, wherein said placing is effective to draw such solution into the unplugged tubes by capillarity.

3. The method of claim 1, wherein said array is a two-dimensional array containing at least 500 tubes.

4. The method of claim 2, wherein said tubes have inner diameters no greater than about 50 μm.

5. The method of claim 1, wherein said plugging includes (i) drawing into one end region of the tubes in said array, a polymerizable solution that can be applied as a liquid and converted to a solid polymer plug by addition of a polymer initiator (ii) selectively injecting polymer initiator into the tubes in the complementary subset, thereby to form polymer plugs in the tubes in the complementary subset, and (iii) removing non-polymerized material from tubes in the selected subset.

6. The method of claim 5, wherein said injecting is carried out by an ink jet printer head.

7. The method of claim 5, wherein said polymerizable solution is an acrylamide/bisacrylamide solution, and said injecting includes selectively injecting a persulfate initiator solution into the tubes in said complementary subset of tubes.

8. The method of claim 4, wherein said plugging includes (i) drawing an radiation-polymerizable solution into one end region of the tubes in said array, (ii) selectively irradiating tubes in the complementary subset, thereby to form polymer plugs in the tubes in the complementary subset, and (iii) removing non-polymerized material from tubes in the selected subset.

9. The method of claim 1, for use in forming a combinatorial library of different-sequence oligonucleotides or oligopeptides, wherein, at each subunit addition step, the array is divided into four separate selected subsets, each of whose tubes are to receive one of four different protected nucleotides, for oligonucleotide synthesis, or are divided into N separate selected subsets, each of whose tubes are to receive one of N different protected amino acids, for oligopeptide synthesis.

10. Apparatus for producing a position-addressable combinatorial library of different-sequence oligomer or different-substituent small molecule compounds in an array of capillary tubes, comprising (i) means for selectively plugging each tube end in a subset of tubes which is complementary to a selected subset of tubes in said array, (ii) means for drawing a selected reagent solution into unplugged tubes in the selected subset of tubes in the array, thereby to effect a compound-addition reaction directly on the inner surface of tubes in the selected subset;

(iii) means for removing the reagent solution from the tubes in the selected subset after said reaction, and for unplugging the tubes in the complementary subset, and (iv) means for repeating the steps performed by elements (i)-(iii) until a desired library of compounds, one library compound in each tube, is produced.

11. The apparatus of claim 10, wherein said introducing means includes (i) means for applying a polymerizable solution to end regions of all of the tubes in the array, (ii) means for selectively polymerizing the tubes in the array which form a complementary subset with the selected tubes of the array, to plug all of the array tubes except those in the selected subset, and (iii) means for introducing reagent solution by capillarity into the unplugged tubes in the array.

12. The apparatus of claim 11, wherein said polymerizing means includes an ink-jet printer head which is effective to inject a polymerization initiator solution into the tubes in the complementary subset of tubes in the array.

* * * * *